US009851420B2

(12) United States Patent
Song (10) Patent No.: US 9,851,420 B2
(45) Date of Patent: Dec. 26, 2017

(54) MAGNETIC RESONANCE TRANSMITTER

(71) Applicant: SCHLUMBERGER TECHNOLOGY CORPORATION, Sugar Land, TX (US)

(72) Inventor: Yi-Qiao Song, Newton, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 900 days.

(21) Appl. No.: 13/963,826

(22) Filed: Aug. 9, 2013

(65) Prior Publication Data

US 2015/0042337 A1 Feb. 12, 2015

(51) Int. Cl.
*G01R 33/36* (2006.01)
*G01R 33/34* (2006.01)
*G01N 24/08* (2006.01)

(52) U.S. Cl.
CPC .......... *G01R 33/34* (2013.01); *G01N 24/081* (2013.01); *G01R 33/3607* (2013.01); *G01R 33/3635* (2013.01); *G01R 33/3664* (2013.01)

(58) Field of Classification Search
CPC  G01R 33/34; G01R 33/3607; G01R 33/3635; G01R 33/3664; G01N 24/081
See application file for complete search history.

(56) References Cited

U.S. PATENT DOCUMENTS

| 4,350,955 | A | 9/1982 | Jackson et al. |
| 5,047,992 | A | 9/1991 | Howlett |
| 5,629,623 | A | 5/1997 | Sezginer et al. |
| 5,903,150 | A | 5/1999 | Roznitsky |
| 6,294,917 | B1 | 9/2001 | Nichols |
| 6,392,410 | B2 | 5/2002 | Luong et al. |
| 6,919,723 | B2 | 7/2005 | Davis |
| 6,943,551 | B2 | 9/2005 | Eberler et al. |
| 7,117,752 | B2 | 10/2006 | May |
| 7,501,817 | B1 | 3/2009 | Luong et al. |
| 9,091,743 | B2 | 7/2015 | Biber et al. |

(Continued)

FOREIGN PATENT DOCUMENTS

| CN | 102735706 A | 10/2012 |
| CN | 103197268 A | 10/2012 |

OTHER PUBLICATIONS

International Search Report and the Written Opinion for International Application No. PCT/US2014/050286 dated Nov. 21, 2014.

(Continued)

*Primary Examiner* — Gregory H Curran (57) ABSTRACT

A transmitter for a magnetic resonance (MR) system, such as nuclear magnetic resonance (NMR) system, is described herein. The transmitter includes a coil for applying NMR pulse sequences to a substance. The coil includes a first coil section and a second coil section. The first coil section and second coil section pass current in opposite polarity. The transmitter may also include a transmitter circuit for generating the NMR pulse sequences and providing the NMR pulse sequences to the coil. The transmitter circuit includes a first switch that selectively powers the first coil section and a second switch that selectively powers the second coil section. Operation of the first switch and the second switch generates the NMR pulse sequences.

17 Claims, 7 Drawing Sheets

(56) References Cited

U.S. PATENT DOCUMENTS

| | | | |
|---|---|---|---|
| 2008/0258723 A1* | 10/2008 | Abe | G01R 33/5613 |
| | | | 324/307 |
| 2011/0127999 A1 | 6/2011 | Lott et al. | |
| 2011/0152891 A1 | 6/2011 | McLawhorn et al. | |
| 2011/0291655 A1 | 12/2011 | Hamamura et al. | |
| 2012/0001629 A1 | 1/2012 | Hopper et al. | |
| 2013/0193968 A1 | 8/2013 | Biber | |
| 2013/0234705 A1 | 9/2013 | Mandal et al. | |
| 2014/0035578 A1* | 2/2014 | Song | G01V 3/32 |
| | | | 324/309 |

OTHER PUBLICATIONS

International Preliminary Report on Patentability issued in PCT/US2014/050286 dated Feb. 18, 2016. 12 pages.

First Office Action and Search Report issued in Chinese patent application 201480054486.5 dated Jan. 3, 2017. 19 pages.

Second Office Action issued in Chinese patent application 201480054486.5 dated Sep. 21, 2017. 17 pages.

\* cited by examiner

MAGNETIC RESONANCE TRANSMITTER

TECHNICAL FIELD

This disclosure relates to magnetic resonance (MR) systems, and more particularly to MR transmitters.

BACKGROUND

Magnetic resonance (MR) systems can be used to determine properties of a substance. One example of a MR system is a nuclear magnetic resonance (NMR) system. A NMR system performs a NMR measurement by applying a static magnetic field to the substance. The static magnetic field generates an initial magnetization of atomic nuclei within the substance. The NMR system also includes a NMR transmitter with a coil that applies an oscillating magnetic field at a particular frequency to the substance. The oscillating field is composed of a sequence of pulses that tip the magnetization of the atomic nuclei away from the initial magnetization. The NMR pulse sequence can be arranged so that pulses and the static field interact with the nuclei to produce a resonant signal composed of "echoes" within at least a portion of the substance. The resonant signal is detected and then used to determine NMR properties such as $T_1$ relaxation time, $T_2$ relaxation time and attenuation of the signal due to molecular diffusion. These NMR properties can be used to determine the properties of the substance.

In some cases, the NMR pulse sequences are applied to the substance at different frequencies to investigate different portions of a substance in an inhomogeneous magnetic field or to investigate different atomic nuclei. To switch between frequencies, narrowband NMR transmitters use banks of fixed capacitors and mechanical switches that are coupled to the coil. The mechanical switches tune the coil to different frequencies by switching between a pre-set number of fixed capacitors. Such narrowband transmitters suffer from several disadvantages. Firstly, the switching process is slow (e.g., 10-100 ms switching times). Secondly, the switches within the capacitor banks introduce noise into the NMR measurement. Thirdly, a predetermined discrete set of narrowband frequencies can be set because each frequency is dependent on separate capacitors. Fourthly, the frequency switching process introduces dynamics and may not maintain phase coherence of the pulse sequence waveform. Accordingly, narrowband NMR transmitters do not efficiently and effectively switch between frequencies.

SUMMARY

Illustrative embodiments of the present disclosure are directed to a transmitter for a magnetic resonance (MR) system, such as nuclear magnetic resonance (NMR) system. The transmitter includes a coil for applying NMR pulse sequences to a substance. The coil includes a first coil section and a second coil section. The first coil section and second coil section pass current in opposite polarity.

In some embodiments, the transmitter may also include a transmitter circuit for generating the MR pulse sequences and providing the MR pulse sequences to the coil. The transmitter circuit includes a first switch that selectively powers the first coil section and a second switch that selectively powers the second coil section. Operation of the first switch and the second switch generates the MR pulse sequences.

Various embodiments of the present disclosure are also directed to a method for applying MR pulse sequences to a substance. The method includes applying current to a first coil section of a coil and applying current to a second coil section of the coil. The current passes through the coil sections in opposite polarity. In some embodiments, the current is selectively applied to the first coil section using a first switch and the current is selectively applied to the second coil section using a second switch. Operation of the first switch and the second switch generate the MR pulse sequences.

Further illustrative embodiments of the present disclosure are directed to a magnetic resonance (MR) system. The system includes a coil with a first coil section and a second coil section. The first coil section and second coil section are wound in opposite polarity. The system also includes a first transistor coupled to the first coil section that selectively powers the first coil section and a second transistor coupled to the second coil section that selectively powers the second coil section.

BRIEF DESCRIPTION OF THE DRAWINGS

Those skilled in the art should more fully appreciate advantages of various embodiments of the disclosure from the following "Description of Illustrative Embodiments," discussed with reference to the drawings summarized immediately below.

DESCRIPTION OF ILLUSTRATIVE EMBODIMENTS

Illustrative embodiments of the present disclosure are directed to a transmitter for a magnetic resonance (MR) system, such as nuclear magnetic resonance (NMR) system. The transmitter includes a coil for applying NMR pulse sequences to a substance. The coil includes a first coil section and a second coil section. The first coil section and second coil section pass current in opposite polarity. In various embodiments, the transmitter also includes a transmitter circuit for generating the NMR pulse sequences and providing the NMR pulse sequences to the coil. The transmitter circuit includes a first switch that selectively powers the first coil section and a second switch that selectively powers the second coil section. Operation of the first switch and the second switch generates the NMR pulse sequences. In this manner, various embodiments of the coil and transmitter circuit are able to transmit NMR pulses sequences over a wide frequency range, while also providing for a simplified transmitter circuit design. Details of various embodiments are discussed below.

Figure 1:
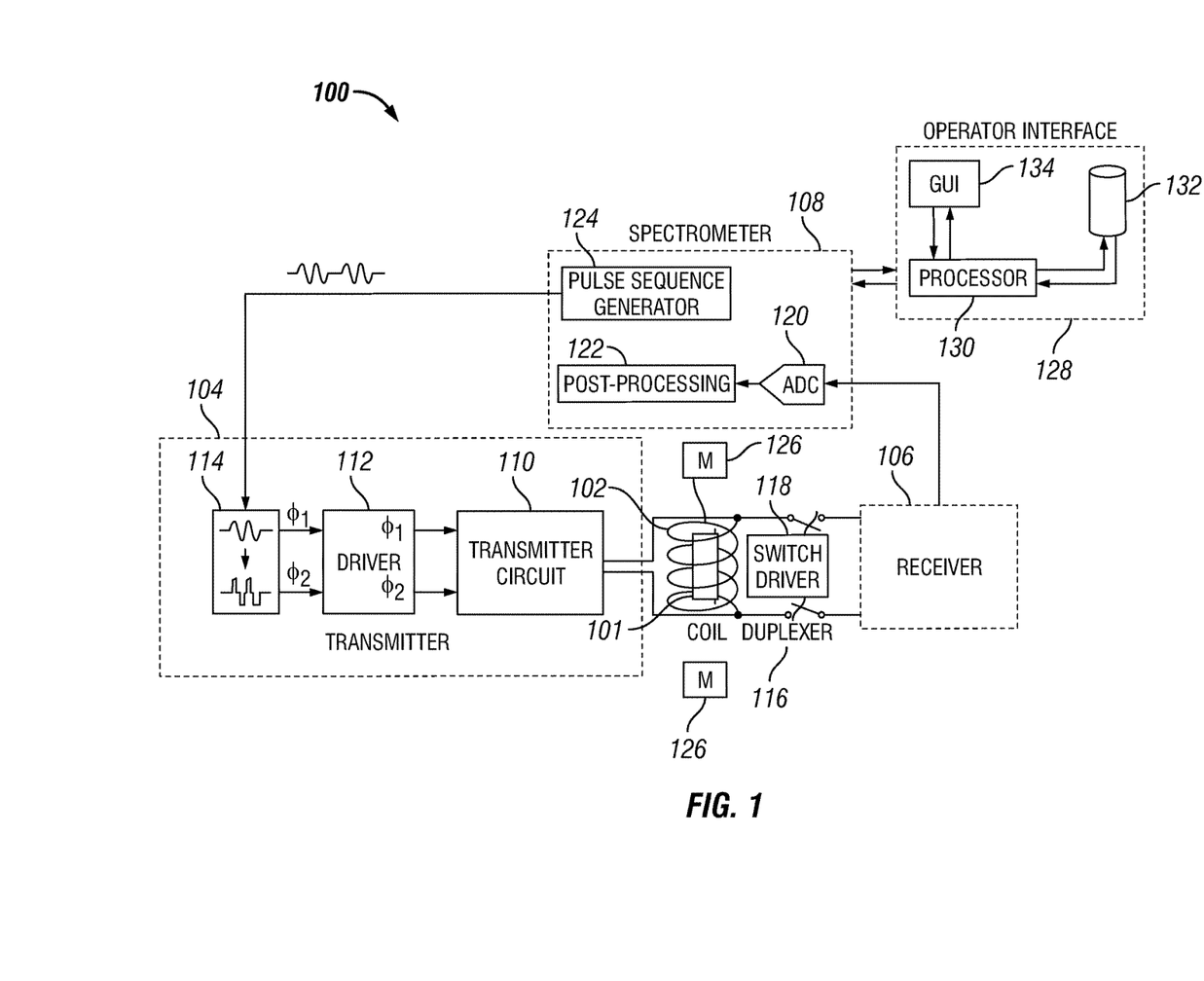
FIG. 1 shows a NMR system in accordance with one embodiment of the present disclosure.

FIG. 1 shows a NMR system 100 in accordance with one embodiment of the present disclosure. The NMR system 100 includes a coil 102 that is coupled to NMR electronics 104, 106, 108. A sample substance 101 is located inside and/or outside of the coil 102. The coil 102 applies NMR pulse sequences to the substance 101. The NMR electronics include a transmitter 104 and a receiver 106. Each of the transmitter 104 and the receiver 106 are coupled to the coil 102. In some embodiments, however, the NMR system 100 may include separate transmitter and receiver coils.

Figure 2:
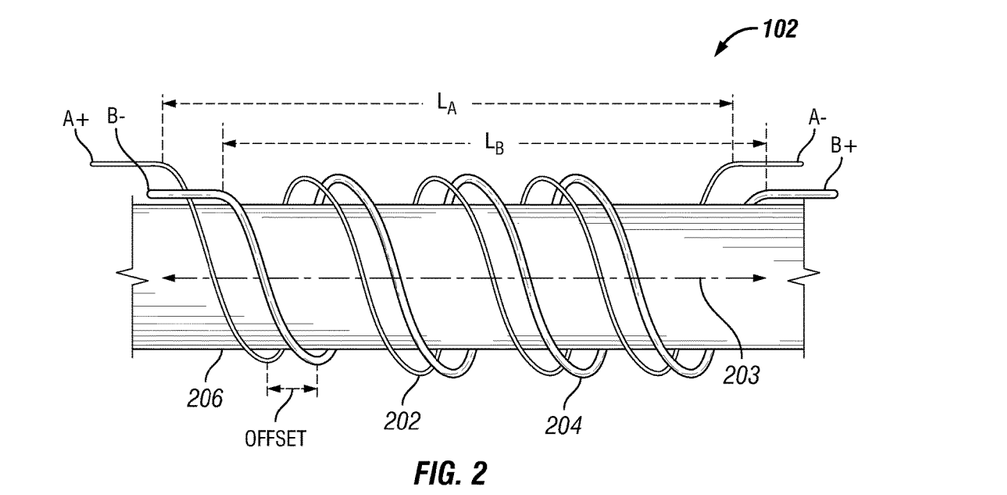
FIG. 2 shows a coil in accordance with one embodiment of the present disclosure.

FIG. 2 shows a detailed view of the coil 102. The coil 102 includes a first coil section 202 and a second coil section 204 that each includes a plurality of windings along a longitudinal axis 203 of the coil. In this embodiment, each coil section is wound around a core element 206. Each coil section has a particular winding length $L_A$ and $L_B$ along the longitudinal axis 203 of the coil 102 and the winding lengths overlap along the length of the longitudinal axis 203. The first coil section 202 includes connections A+ and A− at its ends, while the second coil section 204 includes connections B+ and B− at its ends. The first coil section 202 and second coil section 204 pass current in opposite polarity. For example, in one embodiment, connections A+ and B+ of the coil sections are coupled to a one terminal of a power source, while ends A− and B− of the coil sections are coupled to another terminal of the power source. In this manner, the coil sections pass current in opposite directions along the length of the core element 206.

Figure 3:
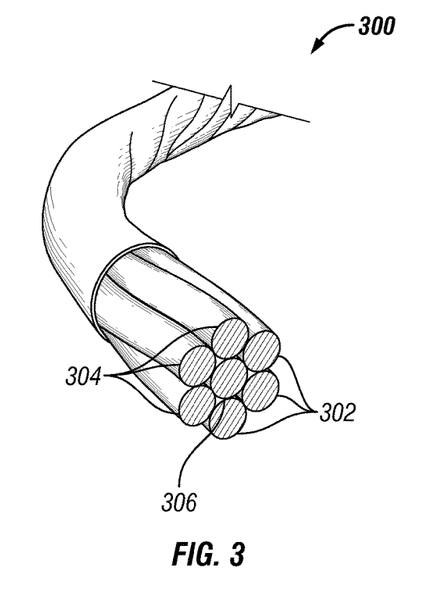
FIG. 3 shows a cable with multiple wire strands.

In some embodiments, the individual windings of the coil sections are offset from each other, as shown in FIG. 2. In other embodiments, the individual windings of the coil sections overlap. For example, in one embodiment, the coil sections are made from a cable with multiple insulated strands, such as a litz cable. FIG. 3 shows an example of a cable 300 with multiple wire strands that are insulated from each other. Three of the seven wire strands are dedicated to the first section of the coil 302 and three other wire strands are dedicated to the section of the coil 304. The remaining wire strand can be dedicated to neutral 306.

Figure 4:
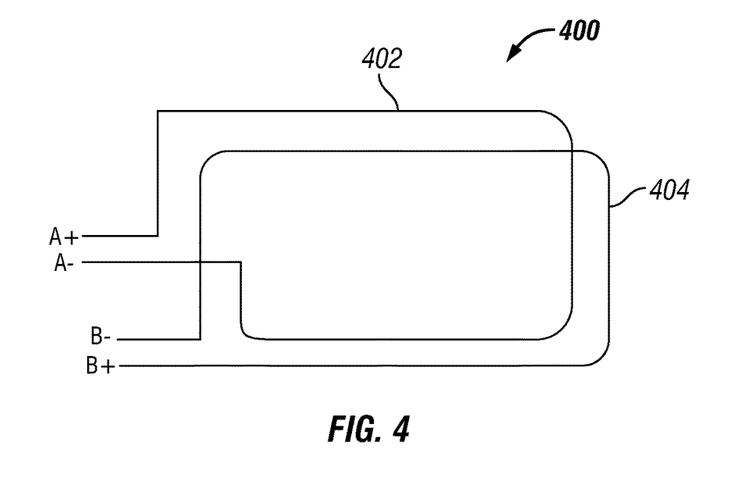
FIG. 4 shows a coil in accordance with another embodiment of the present disclosure.

The coil and coil sections are not limited to any particular dimensions or configurations. For example, each coil section may have between 2 and 20 windings. Also, the winding length of each coil section can be between 1.3 cm and 13 cm and the cross section of the coil can be between 6.5 cm$^2$ and 645 cm$^2$. The coil and coil sections are also not limited to the configuration shown in FIG. 2. For example, FIG. 4 shows a coil 400 with a planar configuration. The planar configuration also includes a first coil section 402 and a second coil section 404. In illustrative embodiments, each coil section may have 1 to 10 loops in this planar configuration. The connection points at A+ and A− are separated in distance from the connection points for B− and B+ to avoid electrical noise between the connections.

The NMR transmitter 104 also includes a NMR transmitter circuit 110 that is coupled to the coil 102. The transmitter circuit 110 generates NMR pulse sequences and provides the NMR pulse sequences to the coil 102. The transmitter circuit 110 is "non-resonant" because the resonant frequency of the circuit does not need to match the Larmor frequency of interest. In contrast, as explained above, narrow-band circuits set their resonant frequencies to match the Larmor frequency of interest by selecting a particular capacitance for the circuit. Although the non-resonant transmitter circuit 110 and coil 102 may use capacitors and have some associated capacitance, this capacitance is not specifically selected to match a Larmor frequency of interest.

Figure 5:
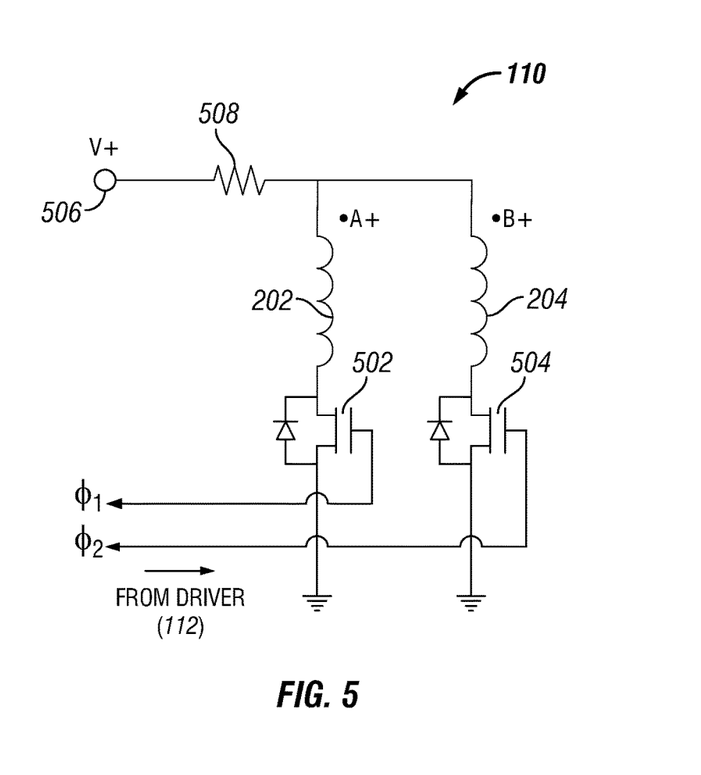
FIG. 5 shows a transmitter circuit in accordance with one embodiment of the present disclosure.

FIG. 5 shows a transmitter circuit 110 in accordance with one embodiment of the present disclosure. The NMR transmitter circuit 110 includes two switches 502 and 504. The first switch 502 is coupled to the first coil section 202 and configured to selectively power the first coil section. The second switch 504 is coupled to the second coil section 204 and configured to selectively power the second coil section. Each switch and corresponding coil section is arranged in parallel. In one particular embodiment, the switches 502, 504 are transistors, such as metal-oxide-semiconductor field-effect transistors (MOSFET), insulated gate bi-polar transistors (IGBT), or various other switches based upon the high frequency switching (HFS) family. In various embodiments, the switches can switch at less than 10 ns.

The transmitter circuit 110 may also include a power source (e.g., a high power supply) 506 that is selectively coupled to the first coil section 202 via the first switch 502 and selectively coupled to the second coil section 204 via the second switch 504. The power source 506 provides current to the first coil section 202 and the second coil section 204 at a particular voltage. Connections A+ and B+ of the coil sections 202, 204 are coupled to a positive terminal of the power source 506, while ends A− and B− of the coil sections are coupled to the switches 502, 504, which are then coupled to ground. Although not shown in FIG. 5, the coil sections 202, 204 are arranged in opposite polarity as shown in, for example, FIG. 2. The circuit 110 may also include a load resistor (R) 508 or fuse that can be used in series with the power source 506 to limit current that is applied to the switches 502, 504.

By selectively coupling the coil sections 202, 204 to the power source 506, the switches 502, 504 control the timing of current flow within each section of the coil. Turning these switches 502, 504 on and off using a certain switching logic generates a current in the coil 102 and thus produces radio frequency irradiation. In this manner, the operation of the switches 502, 504 generates radio frequency pulses and the NMR pulse sequences.

Figure 6:
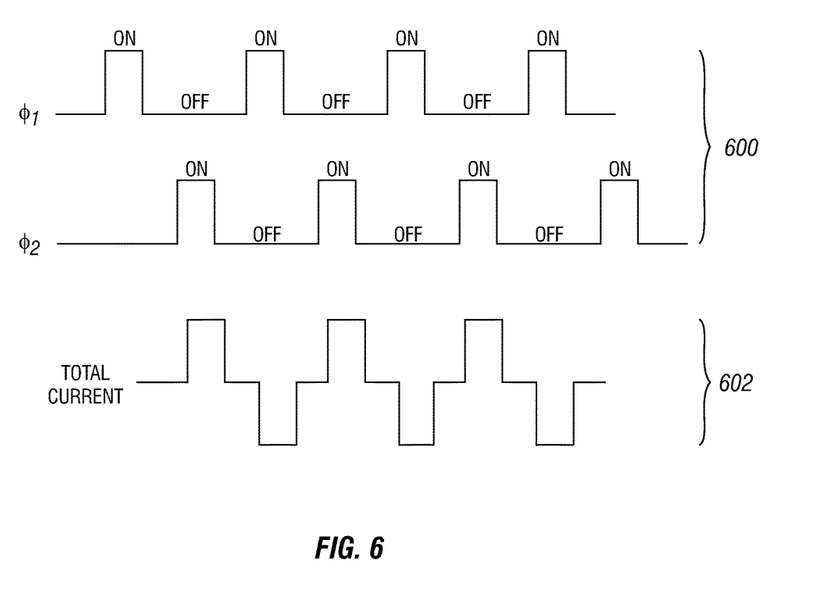
FIG. 6 shows switching logic in accordance with one embodiment of the present disclosure.

FIG. 6 shows an example of switching logic 600 used to operate the first switch 502 and the second switch 504. In this case, the switching logic includes a set of two non-overlapping digital signals denoted as $\phi_1$ and $\phi_2$. The signals $\phi_1$ and $\phi_2$ are used to operate each switch. The first signal $\phi_1$ operates the first switch 502, while the second signal $\phi_2$ operates the second switch 504. The switching logic often includes a period of positive current (or negative current) produced by turning a switch "on" followed by a period of no current produced by turning the switch "off." In various embodiments, the switching logic alternates between injection of current into each coil section 202, 204, as shown in FIG. 5, and, in this manner, produces an alternating current within the coil 102. The total current produced by the coil sections can be determined according to the following relationship:

$$I_T = |I_A| - |I_B|, \quad (1)$$

where $I_T$ is the total current through the coil, $I_A$ is the current through the first coil section and $I_B$ is the current through the second coil section. The current within one coil section subtracts from the other because the coil sections are wound in the opposite polarity. FIG. 6 shows total current 602 within the coil 102 produced by the switching logic 600. As shown in the figure, the switching logic produces a sinusoidal waveform within the coil 102. Repeating the switching logic at a given frequency generates radio frequency power and NMR pulse sequences at a particular frequency. In this case, the waveform is shown as a square waveform. The waveform may also have other shapes (e.g., triangular) depending on coil inductance and resistance within the coil and transmitter circuit.

The transmitter 104 also includes a driver 112 that is coupled to the transmitter circuit 110. In one particular embodiment, the driver 112 can be a computer processor. The driver 112 is used to control operation of the switches 502, 504 within the transmitter circuit 110. As shown in FIG. 5, each switch 502, 504 is also coupled to the driver 102 so that the driver can control the operation of the switches. The driver 112 switches the switches 502, 504 according to a switching logic (e.g., $\phi_1$ and $\phi_2$). In various embodiments, the driver 112 also receives NMR pulse sequences from an NMR spectrometer 108. In some embodiments, the NMR pulse sequences are sent along a plurality of channels. An adder circuit (not shown) can be used to combine the plurality of channels. Also, in various embodiments, the transmitter 104 includes a comparator 114 for receiving the NMR pulse sequences from the spectrometer 108 and generating a square waveform that is provided to the driver 112. The NMR pulse sequences can be translated by the driver 112 into the particular switching logic by selecting waveforms of the NMR pulse sequences and then conditioning the waveforms to an appropriate voltage.

Illustrative embodiments of the NMR transmitter described herein can switch between frequencies that are outside a natural resonant frequency bandwidth of a coil with a tuned circuit. In other words, the NMR transmitter does not depend on tuning a coil to set a particular frequency. In contrast to narrowband systems, which use mechanical switches and banks of fixed capacitors to tune the coil, various embodiments of the transmitters described herein achieve multi-frequency operation without a need for hardware modulation (e.g., switching between fixed capacitors or tuning between variable capacitors). Instead, the frequency can be modulated directly by a spectrometer. The NMR transmitter is frequency insensitive and allows the pulse sequence frequency to be dynamically varied by the spectrometer while maintaining phase coherence of an output waveform. In some cases, the transmitter (and coil) can switch between frequencies with a frequency difference as great as 10% of an initial applied frequency. In various other embodiments, the frequency can be even greater (e.g., 20% 30% or 50%). Also, in some embodiments, the transmitter can switch between frequencies in less than 5 µs. In yet further embodiments, the transmitter can switch between frequencies in less than 20 µs or 50 µs. Furthermore, in some embodiments, the transmitter can operate within a frequency range of 100 kHz and 3.2 MHz.

Various embodiments of the present disclosure also provide for a simplified transmitter design. As shown in FIG. 5 the transmitter circuit uses two switches that are both coupled to ground. This arrangement reduces component count within the transmitter circuit and also provides for simplified switching logic and a simplified driver. For example, a high-voltage driver circuit is not necessary because the two switches are both coupled to ground. Furthermore, by configuring the coil sections in opposite polarity, a single power supply can be used to power both coil sections, while the coil itself produces both a "positive" and a "negative" current.

As shown in FIG. 1, the coil 102 is also coupled to a NMR receiver 106 so that NMR resonant signals that are generated within the substance 101 can be detected, amplified and analyzed. In one specific embodiment, the receiver 106 is a broadband NMR receiver, which can receive and process resonant NMR signals over a broad frequency range. The coil 102 is coupled to the receiver 106 using a duplexer 116. The duplexer 116 decouples the receiver 106 from the coil 102 when the coil is operating in a transmitting mode (e.g., transmitting an NMR pulse sequence). In one particular embodiment, the duplexer 116 includes switches and a switch driver 118 that opens the switches during a transmitting mode and closes the switches during a receiving mode of operation. In this manner, the duplexer 116 protects the receiver 106 during a transmitting mode. A duplexer may not be used when the NMR system 100 includes separate transmit and receive coils.

The NMR system also includes a spectrometer 108 that is used to provide NMR pulse sequences to the NMR transmitter 104 and to analyze the NMR signal received from the NMR receiver 106. In various embodiments, the detected NMR signal is output by the NMR receiver 106 in analog form. In such embodiments, the spectrometer 108 may include a digitizer 120 (e.g., analog-to-digital converter) for converting the detected NMR signal into digital data. Furthermore, in various embodiments, demodulation of the NMR signal can occur within the spectrometer 108. In various other embodiments, however, demodulation of the NMR signal can also occur within the NMR receiver 106. The spectrometer 116 also includes a post-processor 122 that is used to interpret the detected digital NMR data and to determine NMR properties from the detected data. This data can be presented to a user using an operator interface with a graphical user interface (GUI). The spectrometer 108 also includes a pulse sequence generator 124 that generates NMR pulse sequences based upon parameters selected by an operator at the operator interface. The pulse sequence generator provides the sequences to the NMR transmitter 104. In one particular embodiment, the spectrometer 108 is a KEA™, which can be obtained from Magritek of Aachen, Germany. The spectrometer 108 can be controlled from the operator interface using PROSPA™ software, which can also be obtained from Magritek.

Further details of NMR electronics, NMR transmitters and NMR receivers are described in U.S. Publication No. 2012/0001629 published on Jan. 5, 2012 and U.S. application Ser. No. 13/774,457 filed on Feb. 22, 2013, each of which is incorporated by reference in their entireties.

As shown in FIG. 1, the NMR system 100 includes an electro-magnetic device 126 for applying a static magnetic field to the substance 101. In some embodiments, the electro-magnetic device 126 is a magnet or an array of magnets. The magnets can be formed from a samarium-cobalt (SmCo) magnetic material.

The NMR system 100 also includes an operator interface 128 for communicating with the spectrometer 108. The operator interface 128 includes a computer system. The computer system may include a computer processor 130 (e.g., a microprocessor, microcontroller, digital signal processor, or general purpose computer) for executing any of the methods and processes described herein. The computer system may further include a memory 132 such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The memory 132 can be used to store computer instructions (e.g., computer program code) that are interpreted and executed by the processor 130.

NMR pulse sequences may be implemented as a series of computer instructions (e.g., software or firmware) fixed on a non-transitory tangible medium, such as a computer readable medium (e.g., a memory), or transmittable to the computer system, via a modem or other interface device, such as a communications adapter connected to a network over a tangible medium (e.g., optical or analog communications lines). The series of computer instructions can embody all or part of the NMR pulse sequences. The processor 130 may be configured to retrieve the sequences from the memory 132 and provide instructions to the NMR electronics 104, 106, 108 to apply the sequences to the substance 101. The detected resonant signals may also be communicated from the NMR electronics 104, 106, 108 to the processor 130 for storage on the memory 132.

The operator interface 128 also supports the graphical user interface 134 (GUI) (e.g., a monitor, a touch screen, a mouse, a keyboard and/or a joystick). The GUI 134 allows an operator to control and communicate with the NMR electronics 104, 106, 108. In various embodiments, the operator interface 128 can be used to perform functions selected from the following non-limiting list:

Communicate instructions to the NMR electronics 104, 106, 108 to initiate and/or terminate NMR measurements;
Communicate instructions to change parameters of NMR sequences to the NMR electronics (e.g., pulse amplitude of sequences, pulse lengths, timing between pulses, shape of pulses, and/or frequency of pulses);
Communicate detected NMR signal data from the NMR electronics 104, 106, 108 to the operator interface 128;
Communicate NMR pulse sequences from the operator interface 128 to the NMR electronics 104, 106, 108;
Perform analysis at the operator interface 128 of detected NMR signal data to determine NMR properties of substances;
Display various plots of NMR properties to the operator at the operator interface 128; and
Communicate NMR pulse sequences from the operator interface 128 to the NMR electronics 104, 106, 108.

Illustrative embodiments of the present disclosure are not limited to the NMR system 100 shown in FIG. 1. Various modifications can be made to the system. For example, in one specific embodiment, the NMR electronics 104, 106, 108 include an additional computer system that supports the NMR electronics. In such an embodiment, the NMR electronics 104, 106, 108 and operator interface 128 may include their own communication modules, which provide for communication between the NMR electronics and the operator interface. A communications link between the communication modules can be established using, for example, a hard-wired link, an optical link, acoustic link, and/or a wireless link. By using the communication modules, the NMR electronics 104, 106, 108 and the operator interface 128 can be physically located in two separate locations. For example, in a wellbore application, the NMR electronics 104, 106, 108 can be located downhole, while the operator interface 128 is located at the surface.

Figure 7:
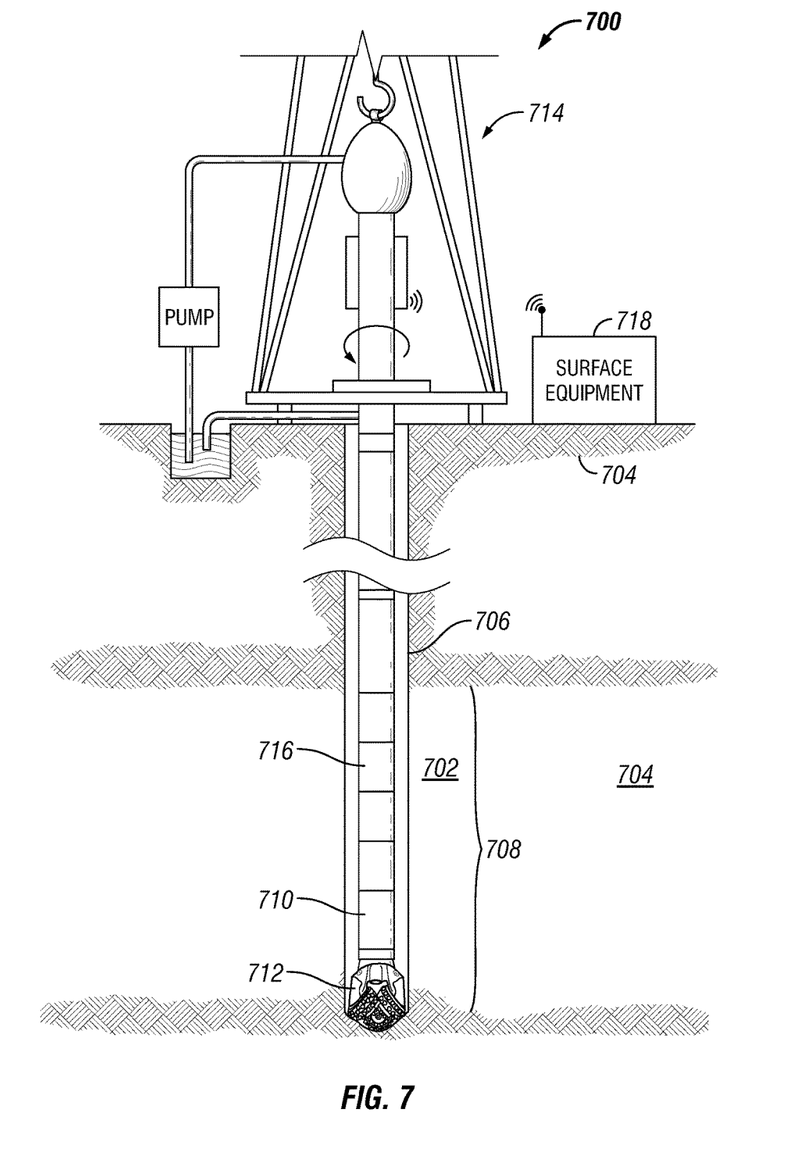
FIG. 7 shows a logging-while-drilling (LWD) system in accordance with one embodiment of the present disclosure.

Illustrative embodiments of the present disclosure are further directed to oil and gas field applications, such as wellbore logging tools. In particular, FIG. 7 shows a logging-while-drilling (LWD) system 700 for investigating, in situ, a substance 702 within an earth formation 704 and determining a property of the substance, while a drilling operation is performed. The LWD system 700 includes a drill string 708. The drill string 708 is disposed within a wellbore 706 that traverses the formation 704. The drill string 708 includes a drill collar 710 with a drill bit 712 disposed at the lower-end of the drill collar. The LWD system 700 also includes a surface system with a derrick assembly and platform assembly 714 positioned over the wellbore 706. The derrick assembly 714 rotates the drill string 708 and, as the drill string rotates, the drill bit 712 drills deeper into the wellbore 706. An LWD NMR logging module 716 is disposed within the drill collar 710 so that the module can log the surrounding earth formation as the drilling operation is performed. The logging module 716 communicates with surface equipment 718, which includes an operator interface for communicating with the module. Such an operator interface has already been described with reference to FIG. 1. In various embodiments, the NMR logging module 716 and operator interface can communicate via any one of a wired-drill pipe connection, an acoustic telemetry connection, optical communication and/or electronic communication.

Figure 8:
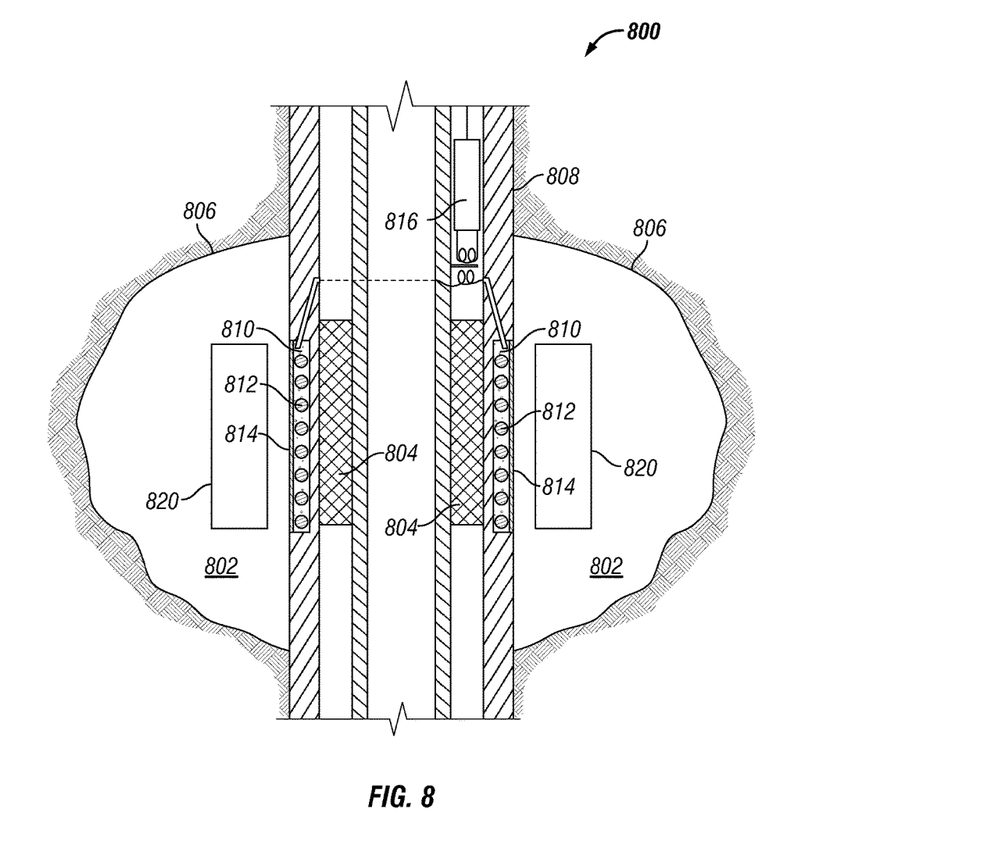
FIG. 8 shows a LWD NMR logging module in accordance with one embodiment of the present disclosure.

FIG. 8 shows an LWD NMR logging module 800 for applying NMR pulse sequences to the formation. The module 800 includes magnet sections 804 that generate a static magnetic field within a zone of sensitivity 806 within the formation 802. The module 800 also includes a drill collar 808 with an axial slot 810. A coil 812 is disposed within the axial slot 810 and the slot is filled with an insulator, such as ceramic, epoxy, or fiberglass. As explained above, the coil 812 includes two coil sections arranged in opposite polarity. The coil sections are wound around the drill collar 808 within the axial slot 812. The axial slot 812 is sealed using a cover 814. In some embodiments, the cover 814 is formed from a non-magnetic material and/or non-conductive material. At one end, the coils sections are grounded (e.g., to the drill collar 808). At the other end, the coil sections are coupled to NMR electronics 816, which include a transmitter with a transmitter circuit, as described in, for example, FIG. 5. The NMR electronics 816 are coupled to the coil 812 via, for example, pressure feed-throughs. The coil 812 applies an oscillating magnetic field (e.g., NMR pulse sequences) to an area of interest 820 within the zone of sensitivity 806 of the formation 802. In some embodiments, the oscillating magnetic field is axially symmetric to facilitate measurements during rotation of the drill string. Further details of NMR LWD systems are described in U.S. Pat. No. 5,629,623 issued on May 13, 1997 and U.S. Pat. No. 6,392,410, issued on May 21, 2002. Each of these patents is incorporated by reference herein in their entireties. One specific example of a NMR LWD tool is Schlumberger's proVISION™ tool.

Figure 9:
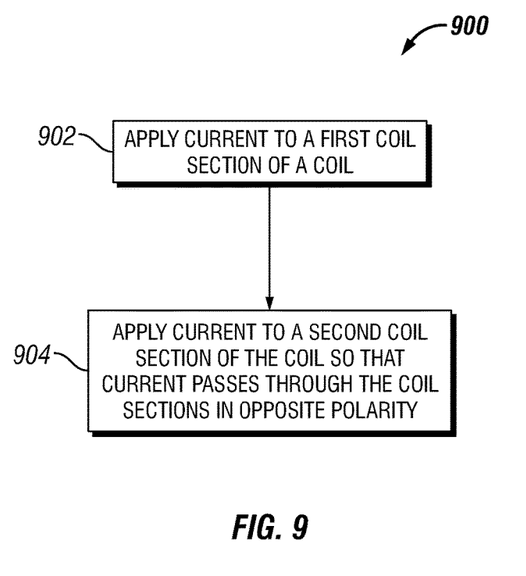
FIG. 9 shows a method for applying radio frequency pulses to a substance in accordance with one embodiment of the present disclosure.

FIG. 9 shows a method 900 for applying radio frequency pulses (e.g., NMR pulse sequences) to a substance. Before the method begins, a substance can be placed within or near a coil for evaluation. At process 902, current is applied to a first coil section of the coil and, at process 904, current is also applied to a second coil section of the coil. The current flows through the coil sections in opposite polarity. As explained above, current is selectively applied to the first coil section using a first switch and current is selectively applied to the second coil section using a second switch. By alternating between injections of current into each coil section, the coil produces an oscillating magnetic field. Processes 902 and 904 are repeated to generate a radio frequency pulse with a specific duration. An NMR pulse sequence includes a series of such pulses of specific duration with delay times between adjacent pulses. The NMR pulse sequences may include, for example, a free-induction decay sequence, a spin echo sequence, a stimulated echo sequence, an inversion recovery sequence, a Can, Purcell, Meiboom and Gill (CPMG) sequence, or some combination sequences. In some embodiments, the NMR signal generated within the substance is detected using the coil. The NMR signal is then used to determine a property of the substance, such as $T_1$ relaxation time, $T_2$ relaxation time and attenuation of the signal due to molecular diffusion.

The NMR transmitters and coils described herein are not limited to any particular device type or system. The NMR transmitters and methods described herein can be implemented in surface environments, such as in a laboratory or in subsurface environments. The NMR transmitters can be used in chemical production, food production, material inspection and infrastructure inspection (e.g., building and bridges).

With respect to wellbore applications, the NMR systems and methods described herein are not limited to LWD systems, such as the one shown in FIGS. 7 and 8. Various embodiments of the present disclosure may also be applied to wireline systems (e.g., a wireline tool) or measuring-while-drilling systems (e.g., MWD tools). In one specific example, a two-section coil with a planar configuration is used as a pad on a wireline tool. Illustrative embodiments can also be used with any suitable means of conveyance, such an armored cable or coiled tubing. Furthermore, the NMR transmitters and methods described herein can be used to investigate a substance within an earth formation outside the wellbore tool (e.g., outside the coil) or to investigate a substance within a flow line or chamber within a wellbore tool (e.g., inside the coil).

The NMR transmitters and coils described herein are not limited to implementing NMR techniques and sequences. The systems and devices described herein can also be used to implement other magnetic resonance (MR) techniques and sequences, such as nuclear quadrupole resonance (NQR) techniques and sequences.

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

What is claimed is:

1. An apparatus comprising:
   a coil for applying magnetic resonance (MR) pulse sequences to a substance, the coil comprising:
   a first coil section having a first winding length along a longitudinal axis of the coil; and
   a second coil section having a second winding length along the longitudinal axis of the coil, wherein the first coil section and second coil section pass current in opposite polarity, and wherein at least a portion of the first winding length overlaps with at least a portion of the second winding length along the longitudinal axis of the coil; and
   a transmitter circuit for generating the MR pulse sequences and providing the MR pulse sequences to the coil;
   wherein the transmitter circuit further comprises
   a first switch coupled to the first coil section and configured to selectively power the first coil section;
   a second switch coupled to the second coil section and configured to selectively power the second coil section.

2. The apparatus of claim 1, wherein the first switch and the second switch comprise transistors.

3. The apparatus of claim 1, wherein the first switch and the second switch are configured to switch in less than 10 ns.

4. The apparatus of claim 1, further comprising:
   a driver coupled to the transmitter circuit and configured to control operation of the first switch and the second switch.

5. The apparatus of claim 4, wherein operation of the first switch and the second switch generates the MR pulse sequences.

6. The apparatus of claim 5, wherein the driver is further configured to control operation of the first switch and the second switch according to a switching logic.

7. The apparatus of claim 1, further comprising:
   a power source selectively coupled to the first coil section via the first switch and selectively coupled to the second coil section via the second switch.

8. The apparatus of claim 1, wherein the apparatus is a component of a wellbore logging tool.

9. The apparatus of claim 8, wherein the first and second coil sections are disposed within an axial slot in a drill collar of the wellbore logging tool.

10. The apparatus of claim 1, wherein a resonant frequency of the transmitter circuit does not match a Larmor frequency of the apparatus.

11. A method for applying radio frequency pulses to a substance, the method comprising:
    applying current to a first coil section of a coil, the first coil section having a first winding length along a longitudinal axis of the coil; and
    applying current to a second coil section of the coil, the second coil section having a second winding length along the longitudinal axis of the coil, wherein current passes through the first and second coil sections in opposite polarity, and wherein at least a portion of the first winding length overlaps with at least a portion of the second winding length along the longitudinal axis of the coil;
    wherein the current is selectively applied to the first coil section using a first switch and the current is selectively applied to the second coil section using a second switch.

12. The method of claim 11, wherein operation of the first switch and the second switch generate the radio frequency pulses.

13. The method of claim 11, wherein the first switch and the second switch are transistors.

14. The method of claim 11, wherein the substance is a formation and the method further comprises:
    applying the radio frequency pulses to the formation.

15. A magnetic resonance (MR) system comprising:
    a coil comprising:
    a first coil section having a first winding length along a longitudinal axis of the coil;
    a second coil section having a second winding length along the longitudinal axis of the coil, wherein the first coil section and second coil section are configured in opposite polarity, and wherein at least a portion of the first winding length overlaps with at least a portion of the second winding length along the longitudinal axis of the coil;
    a first transistor coupled to the first coil section and configured to selectively power the first coil section; and
    a second transistor coupled to the second coil section and configured to selectively power the second coil section.

16. The system of claim 15, further comprising:
    a power source selectively coupled to the first coil section via the first transistor and selectively coupled to the second coil section via the second transistor.

17. The system of claim 15, wherein operation of the first transistor and the second transistor generate the MR pulse sequences.

\* \* \* \* \*